US012594436B2

(12) United States Patent
Schuurman et al.

(10) Patent No.: US 12,594,436 B2
(45) Date of Patent: Apr. 7, 2026

(54) BRACHYTHERAPY SOURCE ASSEMBLY

(71) Applicant: NUCLETRON OPERATIONS B.V., Veenendaal (NL)

(72) Inventors: Jeroen Anton Schuurman, Amersfoort (NL); Frits Pieter De Vries, Renkum (NL); Wim De Jager, Kesteren (NL)

(73) Assignee: Nucletron Operations B.V., Veenendaal (NL)

( * ) Notice: Subject to any disclaimer, the term of this patent is extended or adjusted under 35 U.S.C. 154(b) by 1136 days.

(21) Appl. No.: 17/596,987

(22) PCT Filed: Jun. 25, 2020

(86) PCT No.: PCT/NL2020/050416
§ 371 (c)(1),
(2) Date: Dec. 22, 2021

(87) PCT Pub. No.: WO2020/263091
PCT Pub. Date: Dec. 30, 2020

(65) Prior Publication Data
US 2022/0233881 A1 Jul. 28, 2022

(30) Foreign Application Priority Data

Jun. 27, 2019 (NL) ...................................... 1043317

(51) Int. Cl.
A61N 5/10 (2006.01)
(52) U.S. Cl.
CPC .... A61N 5/1007 (2013.01); *A61N 2005/1024* (2013.01)

(58) Field of Classification Search
CPC ..................................................... A61N 5/1001
See application file for complete search history.

(56) References Cited

U.S. PATENT DOCUMENTS 6,179,768 B1 * 1/2001 Loffler ................. A61N 5/1002
600/7
2009/0216065 A1 * 8/2009 Drobnik ............... A61N 5/1027
600/8

(Continued)

OTHER PUBLICATIONS

"International Application Serial No. PCT/NL2020/050416, International Search Report dated Sep. 21, 2020", (Sep. 21, 2020), 4 pgs.

(Continued)

*Primary Examiner* — Charles A Marmor, II
*Assistant Examiner* — Marc D. Honrath
(74) *Attorney, Agent, or Firm* — Schwegman Lundberg & Woessner, P.A.

(57) ABSTRACT

Embodiments of the disclosure may be drawn to brachytherapy source assemblies. Exemplary source assemblies may include a cable made of an electrically non-conductive material and a guide wire coupled to and extending from a distal end of the cable. The guide wire may have a distal end region and a proximal end region, and the guide wire may have a length that is shorter than a length of the cable. The assembly may also include a capsule located at a distal end region of the guide wire, and the capsule may include a chamber configured to contain a radioactive source. The capsule may be formed of a non-ferromagnetic material and may have a ferromagnetic coating that at least partially covers the capsule.

20 Claims, 4 Drawing Sheets

(56)  References Cited

U.S. PATENT DOCUMENTS

| 2013/0053682 | A1* | 2/2013 | Esthappan | ............... | A61N 5/10 |
| | | | | | 600/411 |
| 2013/0102832 | A1* | 4/2013 | Hoedl | .................. | A61N 5/1001 |
| | | | | | 600/8 |
| 2014/0187849 | A1* | 7/2014 | Bakker | ............... | A61N 5/1007 |
| | | | | | 600/7 |

OTHER PUBLICATIONS

"International Application Serial No. PCT/NL2020/050416, Written Opinion dated Sep. 21, 2020", (Sep. 21, 2020), 5 pgs.

Kos, Sebastian, et al., "MR-guided endovascular interventions: a comprehensive review on techniques and applications", European radiology 18.4, (2008), pp. 645-657.

Tanderup, Kari, et al., "MRI-guided brachytherapy", Semin Radiat Oncol. 24(3), (Jul. 2014), 21 pgs.

Tharmalingam, H., et al., "The role of magnetic resonance imaging in brachytherapy", Clinical Oncology 30.11, (2018), pp. 728-736.

* cited by examiner

CORONAL: MAGNITUDE

REAL

IMAGINARY

PHASE

SAGITTAL: MAGNITUDE

REAL

IMAGINARY

PHASE

BRACHYTHERAPY SOURCE ASSEMBLY

PRIORITY APPLICATIONS

This application is a U.S. National Stage Filing under 35 U.S.C. § 371 from International Application No. PCT/NL2020/050416, filed on Jun. 25, 2020, and published as WO2020/263091 on Dec. 30, 2020, which claims the benefit of priority to Netherlands Application No. 1043317, filed on Jun. 27, 2019; the benefit of priority of each of which is hereby claimed herein, and which applications and publication are hereby incorporated herein by reference in their entireties.

TECHNICAL FIELD

The present disclosure generally relates to brachytherapy and, specifically, to a brachytherapy source assembly designed for use across imaging modalities.

BACKGROUND

During high dose-rate (HDR) brachytherapy treatment, a radioactive brachytherapy source is introduced into or adjacent to a target volume of a patient, for example, a tumor. The radioactive source may be delivered manually or by using an afterloader device. Generally, the afterloader device is used for providing the radioactive source or sources inside the patient for a given period of time at pre-determined dwell positions. Typically, stainless steel cables and capsules make up the brachytherapy source assembly for use with an afterloader. It is difficult, if not impossible, to use stainless steel or other metals in brachytherapy source assemblies while using magnetic resonance imaging (MRI), because a stainless steel capsule may produce large artefacts and obscure the MR image. The use of a stainless steel cable may act as an antenna for the MRI radio frequencies (RF), and the RF may flow into the MRI bore and disturb or obstruct the MRI, and/or generate heat in the stainless steel cable, which may in turn harm and/or burn the patient. Additionally, it may be difficult to determine whether the source is positioned correctly—and thus to determine whether the radioactive source is introduced to the correct target area—because of the large artefacts produced by the stainless steel cable and RF.

SUMMARY

Embodiments of the disclosure may be drawn to brachytherapy source assemblies. Exemplary source assemblies may include a cable made of an electrically non-conductive material; a guide wire coupled to and extending from a distal end of the cable, the guide wire having a distal end region and a proximal end region, and the guide wire having a length that may be shorter than a length of the cable; a capsule located at a distal end region of the guide wire, the capsule including a chamber configured to contain a radioactive source, wherein the capsule may be formed of a non-ferromagnetic material; and a ferromagnetic coating that may at least partially cover the capsule.

Various embodiments of the disclosure may include one or more of the following aspects: the cable may comprise one or more of a plastic material, a ceramic material, metal, or glass fibers; the cable may have a woven outer surface; the source assembly may further comprise an iridium source contained within the capsule; the coating may have a thickness of about 1 μm to about 15 μm; the guide wire may comprise one or more of titanium or aluminum, the capsule may be formed of one or more of titanium, aluminum, or austenitic 316 steel, and the ferromagnetic coating may be formed of one or more of nickel or iron oxide; or the guide wire may have a length of about 10 cm to about 30 cm.

Embodiments of the disclosure may also be drawn to source assemblies that may include a cable having a proximal end and a distal end, wherein the cable may be made of an electrically non-conductive material, and wherein a length of the guide wire may be selected to be less than or equal to ⅒ of a radiofrequency wavelength of a magnetic resonance imaging system with which the brachytherapy source assembly may be configured for use; a guide wire having a proximal end coupled to the distal end of the cable, wherein the guide wire may be formed of a non-ferromagnetic material; a capsule having a proximal end coupled to a distal end of the guide wire and defining an interior chamber configured to contain a source, wherein the capsule may be formed of a non-ferromagnetic material; and a ferromagnetic coating covering at least a portion of the capsule; wherein the guide wire may space the capsule away from the cable.

Various embodiments of the disclosure may include one or more of the following aspects: the cable may comprise one or more of a plastic material, a ceramic material, metal, or glass fibers; the capsule may contain the source and the source may be a radioactive source; the radioactive source may be iridium and the radioactive source may have a ferromagnetic coating; the capsule and the guide wire may comprise at least one of titanium or aluminum; the coating may have a thickness of about 1 μm to about 15 μm; the coating may include nickel or iron oxide; the guide wire may have a length of about 10 cm to about 30 cm; or the cable may have a woven outer surface.

Embodiments of the present disclosure may also be drawn to a source assembly that may include a cable having a proximal end and a distal end and comprising one or more of a plastic material, a ceramic material, or glass fibers; a guide wire having a length of about 10 cm to about 30 cm, wherein the guide wire may have a distal end region and a proximal end region coupled to the distal end of the cable; a capsule located at the distal end region of the guide wire, the capsule including a chamber configured to contain a source, wherein the capsule may be one or more of titanium or aluminum; and a nickel or iron oxide coating at least partially covering the capsule, wherein the nickel coating may have a thickness of about 5 μm to about 15 μm.

Various embodiments of the disclosure may include one or more of the following aspects: the cable may include a woven outer surface; the cable may be electrically non-conductive; or the guide wire may be one or more of titanium or aluminum.

Additional objects and advantages of the disclosed embodiments will be set forth in part in the description that follows, and in part will be apparent from the description, or may be learned by practice of the disclosed embodiments.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

For simplicity and clarity of illustration, the figures depict the general structure and/or manner of construction of the various embodiments described herein. For ease of illustration, the figures may depict various components as uniform and smooth shapes. However, a person skilled in the art would recognize that, in reality, the different components may have a non-uniform thickness and/or irregular shapes. Descriptions and details of well-known features and techniques may be omitted to avoid obscuring other features. Elements in the figures are not necessarily drawn to scale. The dimensions of some features may be exaggerated relative to other features to improve understanding of the exemplary embodiments.

Further, one skilled in the art would understand that, even if it is not specifically mentioned, aspects described with reference to one embodiment may also be applicable to, and may be used with, other embodiments. Moreover, there are many embodiments described and illustrated herein. The present disclosure is neither limited to any single aspect nor embodiment thereof, nor to any combinations and/or permutations of such aspects and/or embodiments. Moreover, each aspect of the present disclosure, and/or embodiments thereof, may be employed alone or in combination with one or more of the other aspects of the present disclosure and/or embodiments thereof. For the sake of brevity, certain permutations and combinations are not discussed and/or illustrated separately herein.

Figure 1:
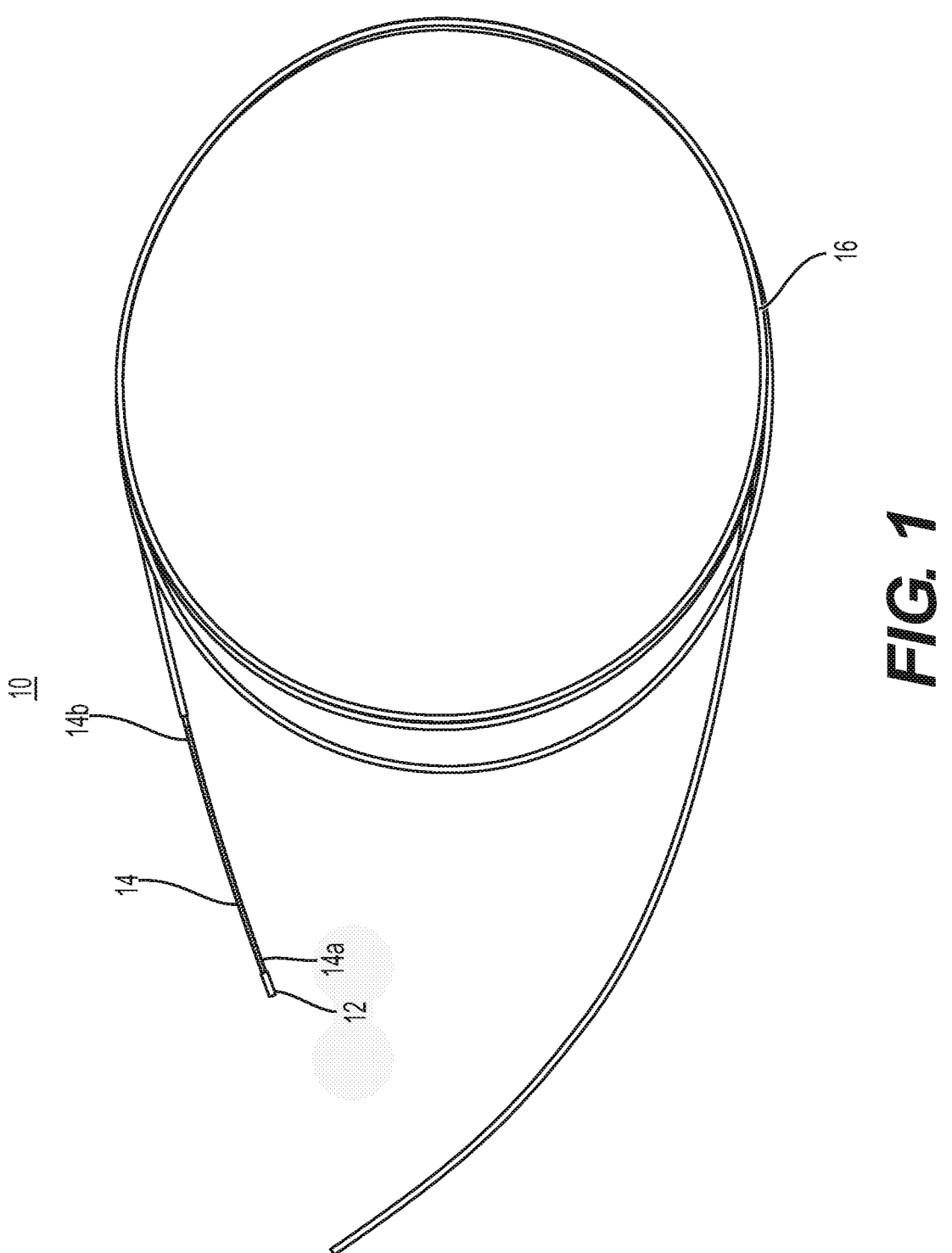
Figure 2:
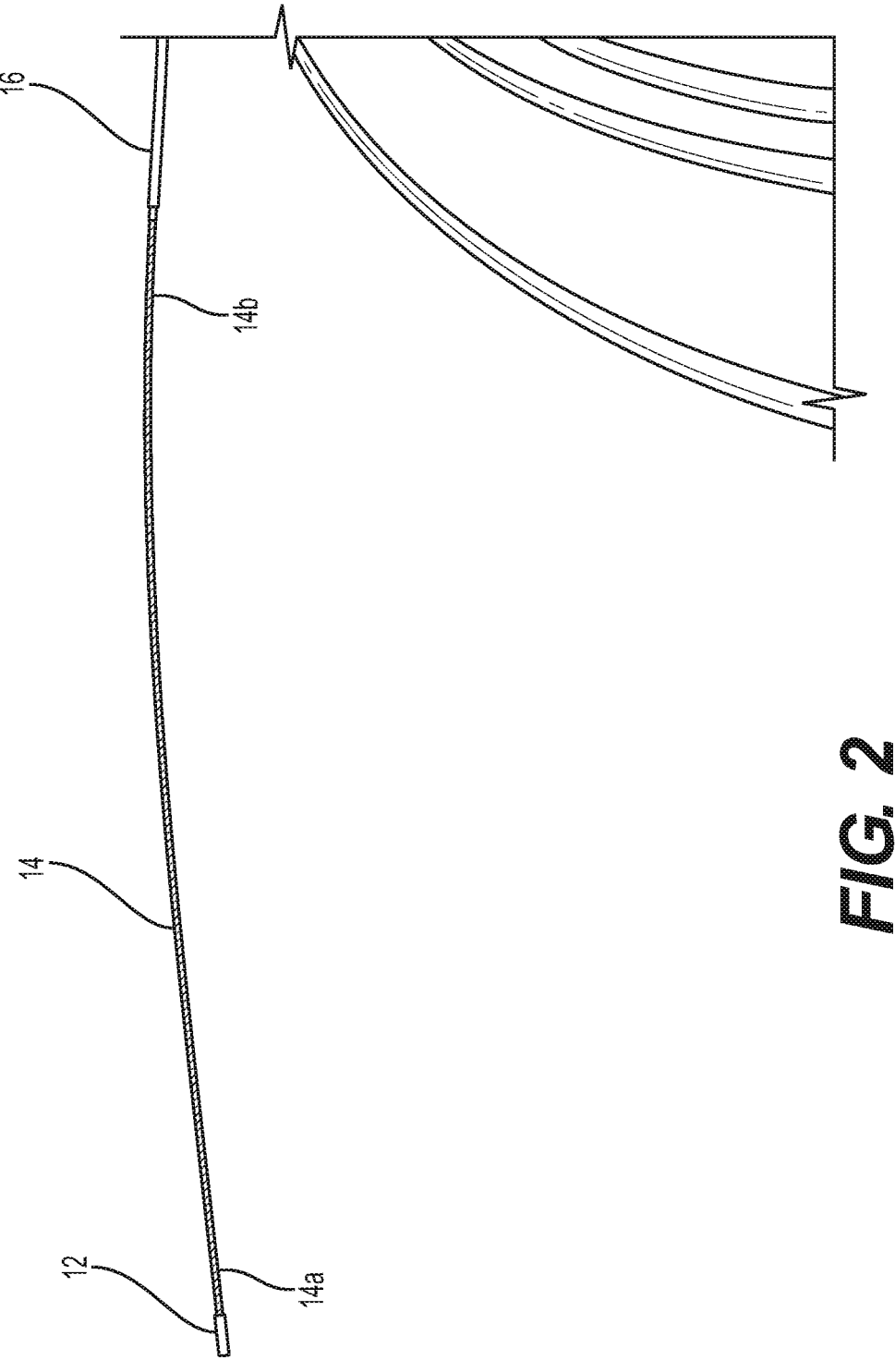
Figure 3:
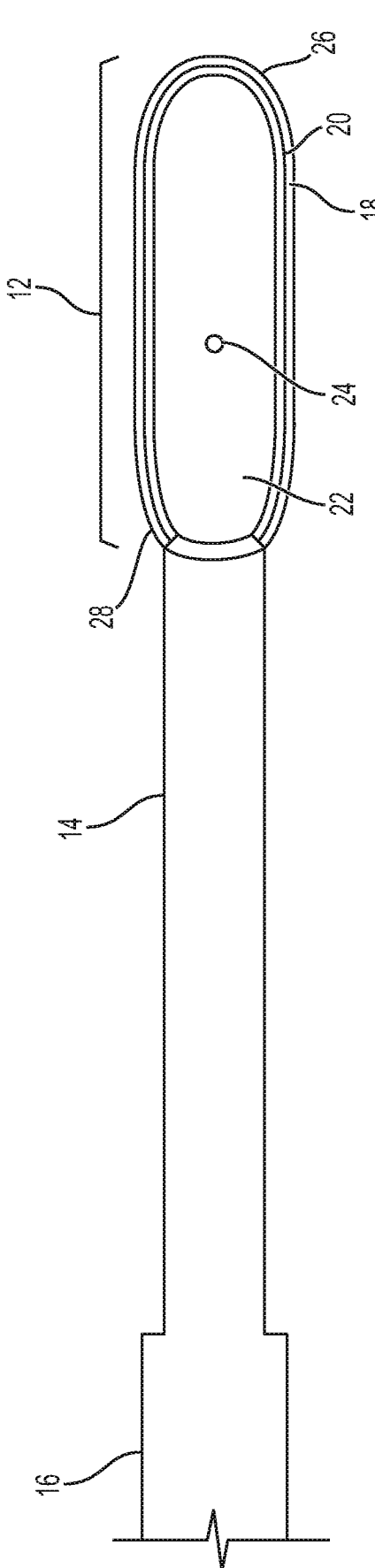
Figures 4A, 4B, 4C, 4D, 4E, 4F, 4G, 4H:
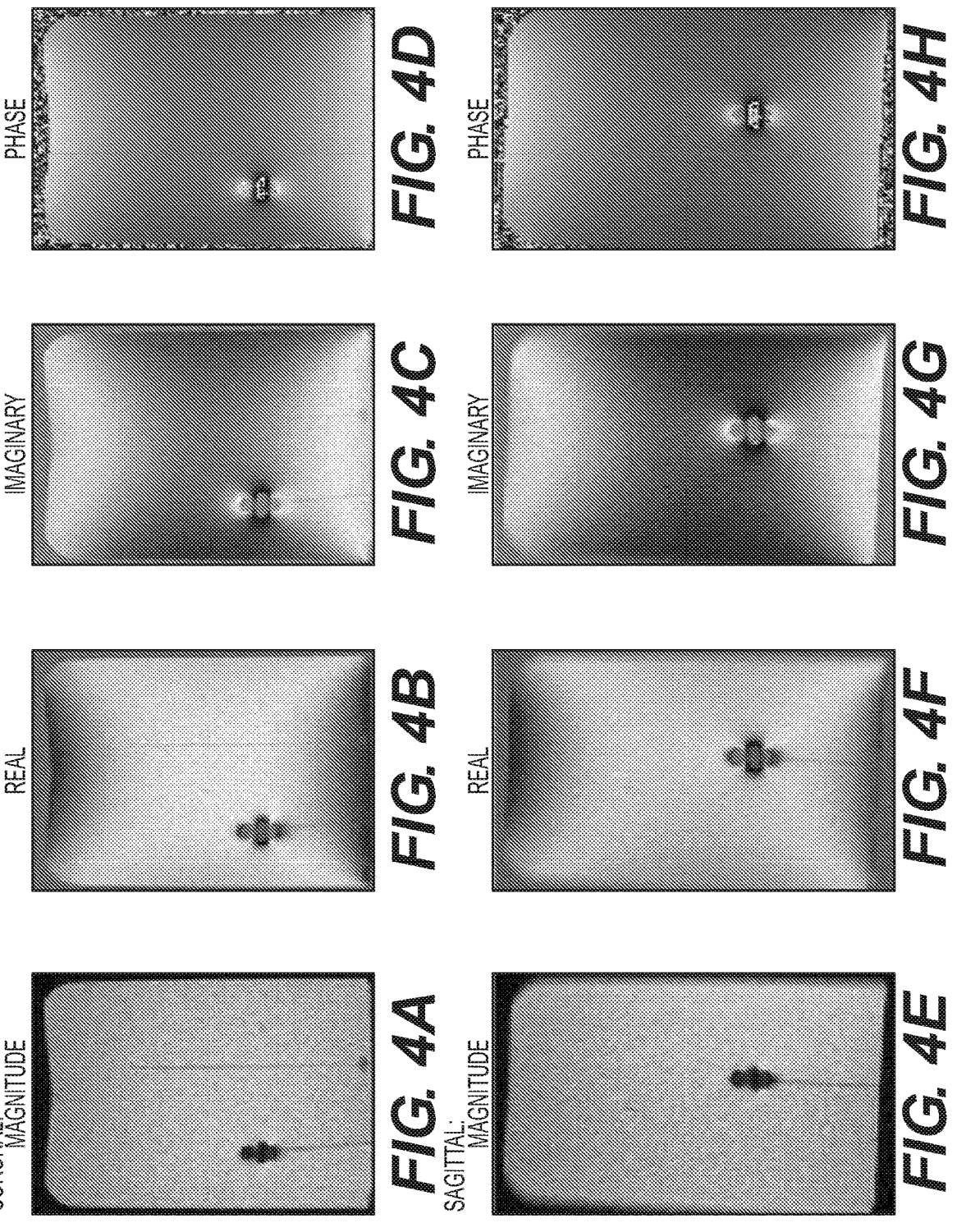

FIG. 1 illustrates an exemplary brachytherapy source assembly according to embodiments of the present disclosure;

FIG. 2 illustrates a close-up view of a portion of the exemplary brachytherapy source assembly of FIG. 1;

FIG. 3 illustrates a cross-sectional view of a capsule, guide wire, and cable of an exemplary brachytherapy source assembly according to embodiments of the present disclosure; and FIGS. 4A-4H illustrate exemplary MRIs of an exemplary brachytherapy source assembly according to embodiments of the present disclosure.

DETAILED DESCRIPTION

It should be noted that the description set forth herein is merely illustrative in nature and is not intended to limit the embodiments of the subject matter, or the application and uses of such embodiments. Any implementation described herein as exemplary is not to be construed as preferred or advantageous over other implementations. Rather, the term "exemplary" is used in the sense of example or "illustrative," rather than "ideal." The terms "comprise," "include," "have," "with," and any variations thereof are used synonymously to denote or describe a non-exclusive inclusion. As such, a device or a method that uses such terms does not include only those elements or steps, but may include other elements and steps not expressly listed or inherent to such device and method. The term "distal" refers to the direction that is away from the user or operator and into the subject. By contrast, the term "proximal" refers to the direction that is closer to the user or operator and away from the subject.

The singular forms "a," "an," and "the" include plural reference unless the context dictates otherwise. The terms "approximately" and "about" refer to being nearly the same as a referenced number or value. As used herein, the terms "approximately" and "about" generally should be understood to encompass ±5% of a specified amount or value. All ranges are understood to include endpoints, e.g., a distance between 1.0 cm and 5.0 cm includes distances of 1.0 cm, 5.0 cm, and all values between.

The term "brachytherapy instrument" shall refer to any device or instrument selected from a group consisting of a radioactive source or a dummy source, a brachytherapy applicator, a cable and/or capsule for moving the radioactive source or the dummy source, a check cable, a rod, a transfer tube, a reinforced rod, a reinforced tube, a needle, a catheter, an obturator, or a guide wire which is used during insertion or during use of a radioactive source or a dummy source. In brachytherapy treatments, the radioactive source is delivered, e.g., via a hollow needle, a flexile tube or cable, a capsule, a catheter, or the like, to the area to be treated. The radioactive source is typically moved through a series of pre-planned and pre-determined dwell positions, where the radioactive source is held at each dwell position for a desired or prescribed range of time.

FIGS. 1-3 illustrate an exemplary brachytherapy source assembly 10 of a brachytherapy instrument. During brachytherapy treatments, a radioactive source is directed towards diseased tissue and is directed away from healthy tissues, to the extent possible. Accordingly, to guide treatment, it may be helpful to use imaging, i.e., computed tomography (CT) and/or MRI, while the source is being delivered to the region of interest and/or while moved along dwell positions. This real-time imaging may greatly improve the accuracy of placing and delivering the source to targeted areas.

Stainless steel and similar materials are often used on cables, wires, and capsules of brachytherapy instruments. The use of such materials may produce large ferromagnetic artefacts, which may distort magnetic fields, thereby causing relatively large and severe obstructions in MR images. Additionally, the RF signals used in MRI may generate heat in the stainless steel cables, wires, and/or capsules, which can harm and/or burn a patient. As a result, traditional source assemblies for use with brachytherapy may not be compatible with MRI, thus limiting the ability of clinicians to use MRI while performing brachytherapy treatment. However, to safely determine whether a brachytherapy source and/or brachytherapy instrument has been correctly placed within a patient, it may be valuable to use static or real-time MRI to confirm correct positioning. Embodiments of the present disclosure are drawn to a source assembly composed of MRI-compatible materials for use with brachytherapy.

FIGS. 1, 2, and 3 illustrate a brachytherapy assembly 10 including a guide wire 14 with a capsule 12 at a distal end region 14a of the guide wire 14, wherein a proximal end region 14b of the guide wire 14 is connected to a non-conductive cable 16. The non-conductive cable 16 may be formed of any suitable material designed to prevent the RF from disrupting the MRI and increasing the temperature of the cable 16, as will be discussed further below. The capsule 12 and guide wire 14 may be formed of non-ferromagnetic or less-ferromagnetic materials to be able to withstand the radiation of a radioactive source within capsule 12 but to also be compatible with MR imaging. Further, the guide wire 14 may provide spacing between the capsule 12 and the cable 16 to reduce the amount of radiation to which cable 16 is exposed. Aspects and details of exemplary brachytherapy assemblies 10 will be described further below.

Referencing FIG. 3, capsule 12 may have a chamber 22 for holding a radioactive source 24. In other embodiments, capsule 12 may be a dummy capsule and may not include a radioactive source 24. The chamber 22 may be a closed chamber. The chamber 22 of the capsule 12 may be defined by one or more walls 20 that surrounds the chamber 22. In some examples, the wall 20 may be a cylindrical mantle that is closed at the distal end of the capsule 12. The distal end 26 of the capsule 12 may have a rounded or blunt shape, e.g., at a distal region, to facilitate passage of capsule 12 through an applicator/catheter.

As discussed above, the capsule 12 may be formed of one or more materials having high strength and resistance to radioactive radiation and low magnetic susceptibility, e.g., non-ferromagnetic metals, such as titanium, aluminum, zirconium, zinc, aluminum zinc magnesium, or combinations of alloys thereof. In some aspects, the capsule 12 may be entirely titanium. In some aspects, capsule 12 may be composed of a ceramic, other than ceramics with iron, cobalt, or nickel compounds, such as ceramics with iron oxide, aluminum oxide, zirconium oxide, silicium carbide, or aluminum titanate. In some examples, the capsule 12 may include a limited amount of a less-ferromagnetic material, such as steel, such that the capsule does not produce a relatively large ferromagnetic artefact in the MRI. For example, a less ferromagnetic steel, like austenitic 316 steel, may be used.

The length of the capsule 12 may range from about 2.0 mm to about 10.0 mm, e.g., from about 2.5 mm to about 8.0 mm, or from about 3.0 mm to about 6.0 mm. The width (or cross sectional diameter) of the capsule may range from about 0.4 mm to about 2.0 mm, e.g., from about 0.5 mm to about 1.5 mm, or from about 0.6 mm to about 1.2 mm. The average wall thickness of the capsule may range from about 25 μm to about 500 μm, e.g., from about 50 μm to about 250 μm.

At least part of the exterior surface of the wall 20 of the capsule 12 may have a ferromagnetic coating 18 formed of, e.g., nickel, iron, cobalt, NiCo, magnetite, or iron oxide, or combinations thereof. In some examples, the exterior surface of the capsule 12 may be completely covered with the coating 18, while in other examples, at least a portion of the capsule 12 may be covered with the coating 18. In some examples, the coating 18 may have a substantially even thickness around the capsule 12, while in others, the coating 18 may be thicker or thinner in one or more regions. The thickness of the coating may range from about 1 μm to about 15 μm, for example, from about 1 μm to about 10 μm, from about 1 μm to about 5 μm, from about 2.5 μm to about 12.5 μm, or from about 5 μm to about 10 μm. For example, the thickness of the coating may be about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, or about 15 μm. Ferromagnetic coatings with an average thickness in these ranges may create a small, recognizable, artefact in an MR image, as is shown in FIGS. 4A-4H and discussed further below. This artefact may assist in locating capsule 12 (and potentially a source housed therein) when using the brachytherapy assembly in conjunction with MR imaging.

Cable 16 may be formed of a non-conductive material, such as a plastic material, ceramic fibers, glass fibers, arylate, zylon, Kevlar, Vectran™ (e.g., a liquid-crystal polymer), or other suitable fibers or wires. Further, a non-conductive and non-ferromagnetic metal, or a combination of metals, may be used. The use of non-conductive materials may stop the import of RF from the afterloader into the MRI bore and may not produce an artefact in the MRI. Whereas traditional brachytherapy cables may be formed of stainless steel and may be incompatible with MRI, forming cable 16 out of one or more strong, non-brittle, high-temperature tolerant, non-conductive materials, like those listed above, may allow embodiments of the present disclosure to be compatible with MRI.

In some aspects, cable 16 may be formed of combinations of materials. For example, if non-ferromagnetic and non-conductive metal is included in cable 16, then the lengths of the metal portions should be below $\frac{1}{10}$ of the RF wavelength of the MRI being used so as to not create too great of an artefact in an MR image or so as to not generate too much heat. For example, for a 1.5 Tesla magnetic field, the length of the metal portion(s) of the cable 16 may be less than or equal to about 47 cm to about 50 cm, and for a 3.0 Tesla magnetic field, the length of the metal portion(s) of the cable 16 may be less than or equal to about 23 cm to about 25 cm. Accordingly, in some aspects, cable 16 may be formed of alternating portions of metal and plastic and/or ceramic and/or glass fiber materials. Or, in other aspects, even if metal is not used to form cable 16, cable 16 may be formed of alternating portions of plastic and/or ceramic and/or glass fiber materials.

Further, in some examples, the cable 16 may be formed of a woven reinforced plastic wire, ceramic fiber, or glass fiber. The use of a woven cable 16 may decrease friction when cable 16 is being passed through, e.g., a transfer tube during brachytherapy. If a non-woven, smooth, plastic cable is used, in some aspects, the friction may become high enough to prevent cable 16 from freely moving through a transfer tube. For example, brachytherapy cables may be, e.g., about 2.5 meters long or more, and such lengths may be incompatible in some instances for use with smooth plastic cables due to high friction. A woven cable of plastic, ceramic, or glass fiber material may reduce friction between the cable and the transfer tube and/or applicator, so that the cable can more easily travel through the transfer tube and applicator.

In conventional brachytherapy cables, a radioactive source may be attached to a distal end of a cable. However, a new problem may be introduced if cable 16 is formed of a non-conductive material like plastic material, ceramic material, glass fibers, or mixtures thereof, because these non-conductive materials may deteriorate when exposed to the radioactive source 24 contained in capsule 12. For example, the radiation emitted from the radioactive source 24 may melt and disintegrate a plastic cable 16. To relieve this problem, a metal guide wire 14 may be incorporated between the cable 16 and the capsule 12 containing the radioactive source 24 so that a distal end of cable 16 is positioned far enough away from radioactive source 24 so as to not compromise the integrity of cable 16 during use. The metal material of guide wire 14 may be resistant to degradation by radioactive source 24.

Accordingly, as shown in FIG. 3, guide wire 14 may separate the capsule 12 configured to contain a radioactive source 24 from the cable 16 to prevent the radiation from disintegrating the cable 16. Guide wire 14 of the present disclosure may have a distal end region 14a attached to the capsule 12 and a proximal end region 14b attached to cable 16. Guide wire 14 may be formed of one or more strong, non-brittle, high-temperature, and/or non-conductive materials, e.g., titanium, aluminum, zirconium, zinc, aluminum zinc magnesium, or ceramics with aluminum oxide, zirconium oxide, silicium carbide, or aluminum titanate, or combinations of alloys thereof. In some examples, the guide wire 14 may be entirely titanium. In some aspects, guide wire 14 may be formed of flexible, strong ceramic or glass fibers.

The capsule 12 may be a separate component from the guide wire 14 and may be attached to guide wire 14, for example, by a crimp joint, a press joint, a click joint, a weld, a coupling sleeve, a glue (adhesive) joint, or other suitable attachment mechanisms. In other exemplary embodiments of the present disclosure, the guide wire 14 may be sealed at a location such as to define the capsule 12 between the sealed location and the distal-most end of the guide wire 14 (not shown). The proximal or distal end of the capsule 12 may be sealed with any appropriate component, such as with a plug. The guide wire 14 may be configured to fit into the afterloader device and transfer tube of the brachytherapy instrument.

The guide wire 14 may be sufficiently long so as to reduce or prevent damage to the cable 16 from the radioactive source 24. However, the guide wire 14 may also not be so long as to cause artefacts in MR images or to generate enough heat so as to potentially injure surrounding tissue. Exemplary lengths of the guide wire 14 may range up to about 15 cm, about 25 cm, about 26 cm, about 27 cm, about 28 cm, about 29 cm, or about 30 cm. The length of the guide wire 14 may range from about 1 cm to about 60 cm, e.g., from about 10 cm to about 50 cm. In some examples, the length of the guide wire 14 may be about 5 cm, about 8 cm, about 10 cm, about 12 cm, about 15 cm, about 20 cm, about 25 cm, about 30 cm, about 35 cm, about 40 cm, about 45 cm, or about 50 cm. The guide wire 14 may have a length of less than or equal to $\frac{1}{10}$ of the RF wavelength of the MRI so as to not create too great of an artefact in an MR image or so as to not generate too much heat. For example, for a 1.5 Tesla magnetic field, the length of the guide wire 14 may be less than or equal to about 47 cm to about 50 cm, and for a 3.0 Tesla magnetic field, the length of the guide wire 14 may be less than or equal to about 23 cm to about 25 cm. The minimum length of guide wire 14 may be that of the radius of the afterloader vault or a thickness of a wall of the vault in which the brachytherapy source is stored when not in use. When the brachytherapy source is stored in the vault of the afterloader, it may be desirable for the guide wire 14 to span the radius of the vault, or at least the thickness of a wall of the vault, so that the non-conductive cable 16 of the assembly remains outside of the vault. In this way, during storage, the non-conductive cable may be shielded from the source radiation so as to better maintain the integrity of the cable. In exemplary afterloaders, the radius of the vault may be, e.g., about 12 cm.

In some embodiments, the guide wire 14 may be a rod or tubing. In other examples, the guide wire 14 may be a thin flexible rod, and the capsule 12 may be formed in a distal end region 14a of the guide wire 14, for example by drilling or forming a chamber within the rod. In examples where the capsule 12 is formed from the distal end region 14a of the guide wire 14, the guide wire 14 may be the same material as the capsule 12. In such examples, part of the guide wire 14 may form the wall 20 of the chamber 22 of the capsule 12. In one exemplary embodiment, guide wire 14 may be formed of stainless steel, which may be secured within the distal end of the cable 16 and may extend distally of the cable 16 to the capsule 12. The mass of stainless steel used for guide wire 14 and/or capsule 12 may be modulated depending on the desired amount of MRI artefact caused by the steel guide wire 14 and/or the capsule 12. The so called $\chi$ in ppm, a measure for the disturbance in the image, may be adjusted by choosing the amount of steel mass in the rod during manufacture.

In some examples, the chamber 22 of the capsule 12 may be closed by means of a plug. In other examples, the plug may be at the proximal end of the capsule 12, i.e., the end of the capsule 12 that is attached to the guide wire 14. The plug may be manufactured from any suitable material, such as an inert metal material, e.g., titanium or stainless steel. The chamber 22 of the capsule 12 may be sealed by welding the plug to the wall 20.

The combination of the capsule 12, guide wire 14, and cable 16 described above may be uniquely suited for use with both CT and MR imaging. Combining a metal capsule 12 as described above on the distal end of a non-conductive cable 16 may generate a limited ferromagnetic artefact in an MR image so that the source position may be reconstructed. The combination of a non-ferromagnetic or less ferromagnetic capsule 12 and guide wire 14 with a ferromagnetic coating may cause a small, but recognizable, artefact in MR images to aid in visualization of the assembly when using MRI, and the non-conductive cable 16 in combination with the non-ferromagnetic capsule 12 may make the assembly compatible for use with MRI.

The radioactive source 24 present in the chamber 22 of the capsule 12 may be any appropriate radioactive source or pellet (collectively "radioactive source 24") used in brachytherapy treatments. For example, the radioactive source may be iridium, californium, cesium, iodine, palladium, phosphorus, radium, ruthenium, samarium, strontium, tantalum, thulium, tungsten, or ytterbium. In some examples, the radioactive source may be iridium 192. In some examples of the present disclosure, the radioactive source 24 may be coated in a ferromagnetic material. For example, the radioactive source 24 may be coated with steel, titanium, nickel, iron oxide, phosphorus, chromium, iron, nickel, cobalt, iron oxide, or combinations of alloys thereof, e.g., NiCr, $TiN_3$, or NiP. The coating of radioactive source 24 may range from about 1 μm to about 60 μm, e.g., from about 5 μm to about 50 μm, from about 10 μm to about 50 μm, from about 5 μm to about 10 μm, from about 10 μm to about 40 μm, or from about 15 μm to about 30 μm. In some examples, the coating may range from about 15 μm to about 25 μm. In some examples, the coating of radioactive source 24 may be about 10 μm, about 20 μm, about 30 μm, about 40 μm, about 50 μm, or about 60 μm. When the radioactive source 24 is present in the chamber 22, it may be in the form of a pellet. The coating on the radioactive source 24 may provide a recognizable, limited, ferromagnetic artefact in an MR image, and/or to prevent dust, and/or to prevent radioactive waste from spreading. In some embodiments, multiple layers of coatings may be used on radioactive source 24.

In other examples, the chamber 22 may be empty. Such an "empty" capsule may be used as a dummy or check cable, e.g., prior to the start of a brachytherapy treatment. The "empty" capsule may be loaded into and out of an applicator or catheter to check the positioning of the applicator or catheter and to check whether any obstructions are present in the path through the applicator or catheter. After having performed this initial check, a capsule containing radioactive material may be loaded into the applicator or catheter in order to carry out the actual brachytherapy treatment.

Various materials, for example, copper, silver, aluminum, silicium, iridium, and gold, may barely produce an artefact on the MRI, and as such, may not alone be adequate for use as a brachytherapy source or a dummy source, because the location of the source, capsule, and/or guide wire, may not be accurately determined. Titanium, platinum, and tungsten, may have slightly higher magnetic susceptibilities, but may not produce a recognizable metal artefact in an MRI. Magnetic susceptibilities of various materials, including those mentioned above, are as follows:

TABLE 1

| Magnetic susceptibility of materials | | |
| --- | --- | --- |
| Water | −13 | patient MRI signal |
| Copper | −5 | |
| Iridium | +25 | radioactive source |
| Tungsten | +58 | CT marker material |
| Platina | +202 | CT and MRI marker material |
| Titanium | +153 | for source capsule |
| Vanadium | +255 | for welding |
| Nickel | ferro | for coating |
| Iron/Steel | ferro | for capsule |

Ferromagnetic materials, e.g., nickel, iron, cobalt, NiCo, magnetite, or iron oxide when used in MRI scans, may produce a small, yet visible artefact, compared to other materials, such as magnetic steel, which may produce a relatively large artefact that may obstruct MR images. Accordingly, using a ferromagnetic, e.g., nickel or iron oxide, coating on the source 24, guide wire 14, and/or the capsule 12 may produce a sufficient artefact so that the location of the source may be determined without obscuring the MRI. The use of titanium, aluminum, or combinations of alloys thereof for the capsule 12, source 24, and/or the guide wire 14, may also produce visible artefacts in CT images. Accordingly, brachytherapy source assemblies of the present disclosure may be used in both MRI and CT/CBCT scans. Iridium, and its decay product Platinum, may be used as a suitable radioactive source because it may not severely obstruct MR images.

When a brachytherapy source assembly according to the present disclosure contains a dummy source instead of a radioactive source, the dummy source may be a non-ferromagnetic material, e.g., copper, titanium, or nitinol, and the dummy source may have a ferromagnetic coating, e.g., a nickel, iron, cobalt, NiCo, magnetite, or iron oxide coating. In some embodiments, a portion of the guide wire 14 may be inserted into the distal end region of the cable 16. The guide wire 14 may extend from the distal end region of the cable 16 to the capsule 12 containing the dummy source, or the guide wire 14 itself may be the dummy source. The guide wire 14 and/or dummy source may be steel, copper, titanium, nitinol, or combinations of alloys thereof. If nickel and/or steel is used in the dummy source, small amounts may be used, to prevent the occurrence of relatively large artefacts. For example, nickel may be present in an amount less than or equal to about 0.05 mg or about 0.10 mg, and steel may be present in an amount less than or equal to about 2.00 mg. For example, non-magnetic austenitic steel 316 may be present in an amount no greater than 2.00 and non-magnetic austenitic steel 304 may be present in an amount no greater than 0.05 mg.

The cable 16 may further include a metal MRI disturbing tip. The MRI disturbing tip may be a capsule of material, such that the guide wire may be glued to a proximal end of the capsule. In another embodiment, a hole may be made in the distal end region of the guide wire 14, such that a small rod of material may be placed into the guide wire 14. The guide wire 14 may be closed by melting the guide wire or gluing the guide wire close. The MRI disturbing tip or small rod may be, e.g., steel, copper, titanium, nitinol, or combinations of alloys thereof. The materials may also have a nickel coating to have a dummy source that may produce a reconstructed ferromagnetic artefact in an MR image.

FIGS. 4A-4H illustrate MR images of an exemplary brachytherapy source assembly according to embodiments of the present disclosure. The capsules have a nickel coating, wherein the coating has a thickness of about 10 μm. The source assembly is connected to a distal end of a plastic cable. The nickel coating produces a small, but visible artefact in the MRI, which indicates the location of the source. To determine the position of the brachytherapy source inside the patient, a coronal and a sagittal 2D MR image of the patient may be taken. FIGS. 4A-4D depict coronal images, and FIGS. 4E-4H depict sagittal images. The position of the source, shown as a small ferromagnetic artefact, may be calculated based on the coronal and sagittal images, e.g., with 2D template matching. For these two images, the coordinates of the brachytherapy source in the 3D MR image may be obtained. The 2D MR image is a complex representation of an image, such that the 2D image exists of a magnitude and phase part, or a real and an imaginary representation of the 2D image. This 2D imaging, template matching, and calculation of the source position may occur quickly and may be measured in real time with 5 Hertz or 10 Hertz repletion time. In some aspects, the limiting time may be the fast 2D MR imaging sequence (T1 weighted sequence with consecutive coronal and sagittal images). In some aspects, template matching may take, e.g., about 40 ms seconds, and calculation of the 3D coordinates may take, e.g., 10 ms seconds. Accordingly, real-time measurements may include measurements taken with a latency of, e.g., about 1,000 ms, about 500 ms, about 250 ms, about 200 ms, about 150 ms, or about 10 ms to about 100 ms. Template matching may be performed with the real or the magnitude image representations showing the artefact. In some aspects, software latencies may be in the order of about 10 ms to about 100 ms.

As described above, exemplary embodiments of the disclosure may make it possible to conduct brachytherapy treatment with MR imaging. With an MRI compatible brachytherapy source, it may be possible to have an afterloader, e.g., Elekta's Flexitron afterloader, and an MRI machine both active and measuring the brachytherapy source position in the patient during brachytherapy treatment in real time or static. With an MRI compatible dummy source as described herein, it may be possible to calibrate the position of an active brachytherapy source and to verify the dwell positions within an implant, applicator, needle, or other suitable device positioned within the patient. Further, it may be possible to calibrate the brachytherapy source position in an MR image so that the source position may be calibrated in the patient imaging system. This may allow steering of the brachytherapy source into the planned dwell positions to be measured and calibrated with a higher precision and/or accuracy than is currently available.

Additionally, with the MRI-compatible devices described herein, it may be possible to perform adaptive brachytherapy treatment. For example, the source position within the patient may be measured in real time, e.g., with real-time MRI, with a sequence of consecutive 2D sagittal and coronal MRI, such as 5 Hertz or 10 Hertz 2D imaging, and if the measured location of the source is different than the intended location of the source, it may be possible to alter and/or to cease the brachytherapy treatment. Or, it may be possible to correct the positioning of the source during the administration of treatment. Overall, it may be possible to visualize the patient, the target treatment area and surrounding anatomy (e.g., tumor and organs), and the brachytherapy source so that the brachytherapy source may be positioned accurately during treatment. As discussed above, the template matching may be performed around 40 μs and the calculation of the 3D coordinates may be done around 10 μs. The real-time MRI may have a timing delay around 250 ms, which may still be sufficient for determining brachytherapy source positioning.

In a further aspect, exemplary embodiments may be directed to a kit of parts comprising a brachytherapy source assembly as described herein and a catheter, flexible tube, or hollow needle for guiding said brachytherapy source assembly to a treatment site.

The present disclosure is also directed to a method for preparing a brachytherapy source assembly, preferably as described herein, wherein said method comprises the steps of having a capsule that includes a chamber configured to contain a radioactive source; applying to at least part of the exterior surface of the wall of the capsule, a nickel coating; and optionally attaching the capsule to a guide wire. In embodiments where the capsule is comprised in the guide wire, the step of providing a capsule may comprise excavating or hollowing out an end portion of a guide wire. Alternatively, the capsule may be provided separately and be attached to a separate guide wire.

The coating may be applied using various deposition techniques known in the art. Suitable techniques include physical vapor deposition (including cathodic arc deposition, electron beam physical vapor deposition, evaporative deposition, pulsed laser deposition, sputter deposition), chemical vapor deposition (including microwave plasma-assisted chemical vapor deposition, plasma-enhanced chemical vapor deposition, remote plasma-enhanced chemical vapor deposition, atomic layer chemical vapor deposition, combustion chemical vapor deposition, hot wire chemical vapor deposition, metalorganic chemical vapor deposition, hybrid physical-chemical vapor deposition, rapid thermal chemical vapor deposition, and vapor phase epitaxy), chemical deposition in liquid baths with or without electrical currents to deposit metals, and deposition welding, such as laser cladding. In some embodiments, plating may also be used.

In yet a further aspect, embodiments of the disclosure may be directed to a brachytherapy treatment comprising applying to an individual in need thereof, a brachytherapy source assembly as described herein. The brachytherapy treatment may be a high dose-rate brachytherapy treatment or, in a special embodiment, a pulsed dose-rate brachytherapy treatment. In a pulsed dose-rate brachytherapy treatment, high dose-rate pulses of treatment that typically last for a period of five to ten minutes) are repeated at short intervals. The intervals may vary, for instance, from once per 30 minutes to once per 3 hours. Typically, the high dose-rate pulses are repeated once per hour.

The invention further pertains to the following examples:

Example 1: A brachytherapy source assembly for delivering brachytherapy treatment, the source assembly comprising:

a cable having a proximal end and a distal end, wherein the cable is made of an electrically non-conductive material;

a guide wire having a proximal end coupled to the distal end of the cable, wherein the guide wire is formed of at least one of a non-ferromagnetic material or austenitic 316 steel, and wherein a length of the guide wire is less than or equal to ¹⁄₁₀ of a radiofrequency wavelength of a magnetic resonance imaging system with which the brachytherapy source assembly is configured for use;

a capsule having a proximal end coupled to a distal end of the guide wire and defining an interior chamber configured to contain a source, wherein the capsule is formed of a non-ferromagnetic material; and a ferromagnetic coating covering at least a portion of the capsule;

wherein the guide wire spaces the capsule away from the cable.

The brachytherapy source assembly of the first example, wherein the cable comprises one or more of a plastic material, a ceramic material, metal, or glass fibers.

The brachytherapy source assembly of the first example, wherein the capsule contains the source, and wherein the source is a radioactive source.

The brachytherapy source assembly of the first example, wherein the radioactive source is iridium, and wherein the radioactive source has a ferromagnetic coating.

The brachytherapy source assembly of the first example, wherein the capsule and the guide wire comprise at least one of titanium or aluminum.

The brachytherapy source assembly of the first example, wherein the coating has a thickness of about 1 μm to about 15 μm.

The brachytherapy source assembly of the first example, wherein the coating includes nickel or iron oxide.

The brachytherapy source assembly of the first example, wherein the guide wire has a length of about 10 cm to about 30 cm.

The brachytherapy source assembly of the first example, wherein the cable has a woven outer surface.

Example 2: A brachytherapy source assembly for delivering brachytherapy treatment, the source assembly comprising:

a cable having a proximal end and a distal end and comprising one or more of a plastic material, a ceramic material, or glass fibers;

a guide wire having a length of about 10 cm to about 30 cm, wherein the guide wire has a distal end region and a proximal end region coupled to the distal end of the cable;

a capsule located at the distal end region of the guide wire, the capsule including a chamber configured to contain a source, wherein the capsule is one or more of titanium or aluminum; and a nickel or iron oxide coating at least partially covering the capsule, wherein the nickel coating has a thickness of about 5 μm to about 15 μm.

The brachytherapy source assembly of the second example, wherein the cable includes a woven outer surface.

The brachytherapy source assembly of the second example, wherein the cable is electrically non-conductive.

The brachytherapy source assembly of the second example, wherein the guide wire is one or more of titanium or aluminum.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted except in light of the attached claims and their equivalents.

What is claimed is:

1. A brachytherapy source assembly for delivering brachytherapy treatment, the source assembly comprising:
   a cable made of an electrically non-conductive material, the cable having a proximal end and a distal end;
   a guide wire having a proximal end coupled to and extending from the distal end of the cable, the guide wire having a distal end region and a proximal end region, and the guide wire having a length that is shorter than a length of the cable; and
   a capsule located at a distal end region of the guide wire, the capsule including a chamber configured to contain a radioactive source, wherein the capsule is formed of at least one of a non-ferromagnetic material or austenitic 316 steel.

2. The brachytherapy source assembly of claim 1, wherein the cable comprises one or more of a plastic material, a ceramic material, metal, glass fibers, or a woven outer surface.

3. The brachytherapy source assembly according to claim 1, wherein the radioactive source includes an iridium source contained within the capsule.

4. The brachytherapy source assembly according to claim 1, further comprising:
   a ferromagnetic coating at least partially covering the capsule.

5. The brachytherapy source assembly of claim 4, wherein the ferromagnetic coating has a thickness of about 1 μm to about 15 μm.

6. The brachytherapy source assembly of claim 4, wherein the guide wire comprises one or more of titanium or aluminum, wherein the capsule is formed of one or more of titanium, aluminum, or austenitic 316 steel, and wherein the coating is formed of one or more of nickel or iron oxide.

7. The brachytherapy source assembly according to claim 1, wherein the guide wire has a length of about 10 cm to about 30 cm.

8. The brachytherapy source assembly according to claim 1, wherein the guide wire is formed of at least one of a non-ferromagnetic material or austenitic 316 steel, wherein a length of the guide wire is less than or equal to ¹⁄₁₀ of a radiofrequency wavelength of a magnetic resonance imaging system with which the brachytherapy source assembly is configured for use, wherein a ferromagnetic coating covers at least a portion of the capsule and wherein the guide wire spaces the capsule away from the cable.

9. The brachytherapy source assembly of claim 8, wherein the capsule and the guide wire comprise at least one of titanium or aluminum.

10. The brachytherapy source assembly of claim 8, wherein the coating has a thickness of about 1 μm to about 15 μm.

11. The brachytherapy source assembly of claim 8, wherein the cable has a woven outer surface.

12. A brachytherapy source assembly for delivering brachytherapy treatment, the source assembly comprising:
   a cable made of an electrically non-conductive material, the cable having a proximal end and a distal end;

a guide wire having a proximal end coupled to and extending from the distal end of the cable, the guide wire having a distal end region and a proximal end region, and the guide wire having a length that is shorter than a length of the cable; and
   a capsule located at a distal end region of the guide wire, the capsule including a chamber configured to contain a radioactive source, wherein the capsule is formed of at least one of a non-ferromagnetic material or austenitic 316 steel, and wherein the radioactive source includes an iridium source contained within the capsule.

13. The brachytherapy source assembly of claim 12, wherein the cable comprises one or more of a plastic material, a ceramic material, metal, glass fibers, or a woven outer surface.

14. The brachytherapy source assembly of claim 12, wherein the guide wire comprises one or more of titanium or aluminum, and wherein the capsule is formed of one or more of titanium, aluminum, or austenitic 316 steel.

15. The brachytherapy source assembly according to claim 12, wherein the guide wire has a length of about 10 cm to about 30 cm.

16. A brachytherapy source assembly for delivering brachytherapy treatment, the source assembly comprising:
   a cable made of an electrically non-conductive material, the cable having a proximal end and a distal end;
   a guide wire having a proximal end coupled to and extending from the distal end of the cable, the guide wire having a distal end region and a proximal end region, and the guide wire having a length that is shorter than a length of the cable;
   a capsule located at a distal end region of the guide wire, the capsule including a chamber configured to contain a radioactive source, wherein the capsule is formed of at least one of a non-ferromagnetic material or austenitic 316 steel, and wherein the radioactive source includes an iridium source contained within the capsule; and
   a ferromagnetic coating at least partially covering the capsule.

17. The brachytherapy source assembly of claim 16, wherein the ferromagnetic coating has a thickness of about 1 μm to about 15 μm.

18. The brachytherapy source assembly according to claim 16, wherein the guide wire is formed of at least one of a non-ferromagnetic material or austenitic 316 steel, wherein a length of the guide wire is less than or equal to ¹⁄₁₀ of a radiofrequency wavelength of a magnetic resonance imaging system with which the brachytherapy source assembly is configured for use, and wherein the guide wire spaces the capsule away from the cable.

19. The brachytherapy source assembly of claim 18, wherein the cable has a woven outer surface.

20. The brachytherapy source assembly of claim 16, wherein the capsule and the guide wire comprise at least one of titanium or aluminum.

* * * * *